(12) United States Patent
Majeed et al.

(10) Patent No.: US 10,085,963 B2
(45) Date of Patent: Oct. 2, 2018

(54) PROCESS AND COMPOSITIONS FOR ACHIEVING MAMMALIAN ENERGY BALANCE

(71) Applicant: SAMI LABS LIMITED, Bangalore (IN)

(72) Inventors: Muhammed Majeed, Edison, NJ (US); Kalyanam Nagabhushanam, East Windsor, NJ (US); Sarang Bani, Bangalore (IN); Anjali Pandey, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 14/936,830

(22) Filed: Nov. 10, 2015

(65) Prior Publication Data

US 2017/0128410 A1   May 11, 2017

(51) Int. Cl.
| | |
|---|---|
| *A61K 31/352* | (2006.01) |
| *A61K 35/35* | (2015.01) |
| *C12N 5/077* | (2010.01) |
| *G01N 33/50* | (2006.01) |

(52) U.S. Cl.
CPC ............ *A61K 31/352* (2013.01); *A61K 35/35* (2013.01); *C12N 5/0653* (2013.01); *G01N 33/5044* (2013.01); *C12N 2501/01* (2013.01); *C12N 2506/13* (2013.01); *G01N 2333/51* (2013.01); *G01N 2333/515* (2013.01)

(58) Field of Classification Search
CPC ..................................................... A61K 31/352
See application file for complete search history.

(56) References Cited

U.S. PATENT DOCUMENTS

| | | | | |
|---|---|---|---|---|
| 2005/0158706 A1* | 7/2005 | Halvorsen | ............... | A61L 27/38 435/4 |
| 2009/0098220 A1* | 4/2009 | Ashworth | .............. | A61K 36/00 424/725 |
| 2013/0012579 A1* | 1/2013 | Majeed | ................ | A61K 31/235 514/543 |

OTHER PUBLICATIONS

Ortmann et al. (Lonza BioResearch, Oct. 15, 2015).*
Georgios Karamanlidis et al., The Journal of Biological Chemistry vol. 282, No. 34, pp. 24660-24669, Aug. 24, 2007. (Year: 2007).*
Angeliki Karamitri et al., The Journal of Biological Chemistry vol. 284, No. 31, pp. 20738-20752, Jul. 31, 2009. (Year: 2009).*

* cited by examiner

*Primary Examiner* — Theodore R. West
(74) *Attorney, Agent, or Firm* — Oliff PLC

(57) ABSTRACT

Disclosed is a method of achieving optimal mammalian energy balance using forskolin on a particular physiological and developmental stage of the mammalian cellular system.

7 Claims, 4 Drawing Sheets

PROCESS AND COMPOSITIONS FOR ACHIEVING MAMMALIAN ENERGY BALANCE

BACKGROUND OF THE INVENTION

Field of the Invention

The invention in general relates to dietary supplements. More specifically, the present invention relates to a method of achieving optimal mammalian energy balance using forskolin on a particular physiological and developmental stage of the mammalian cellular system.

Description of Prior Art

Disruption of mammalian energy balance has been implicated as the cause for worldwide epidemics of metabolic diseases that calls for modifications in life style and food habits and also therapeutic intervention. Current diet regimens, exercise, health care awareness or drug strategies however are often unable to tackle homeostasis of energy in the mammalian body where optimally, a perfect balance between energy accumulation and energy expenditure is sought (Elattar. S and Satyanarayana, "Can Brown Fat Win the Battle against White Fat?", J. Cell Physiol. 2015 Mar. 11, Zafrir B. "Brown adipose tissue: research milestones of a potential player in human energy balance and obesity", Horm Metab Res. 2013 October; 45(11):774-85). An impetus to the understanding of critical biological processes controlling brown adipocyte activity and differentiation has been in vogue in view of developing brown adipose tissue (BAT) focussed therapies for energy homeostasis (Giralt M. "White, brown, beige/brite: different adipose cells for different functions?. Endocrinology. 2013 September; 154(9): 2992-3000) where undue energy abundance is effectively countered by optimal energy expenditure. The present invention discusses the potential of forskolin to mediate mammalian energy balance. Accordingly, it is the principle objective of the present invention to disclose, A. The ability of forskolin to prevent the formation of lipids within adult adipocytes during the differentiation of pre-adipocytes to adipocytes wherein the adipogenesis (fat deposition) inhibition is remarkably enhanced when forskolin is administered (brought into contact) to pre-adipocytes rather than to mature adipocytes;

B. The ability of forskolin to enhance the expression of secreted factors that selectively recruit brown adipose tissue (BAT) like bone morphogenetic protein-7 (BMP-7), bone morphogenetic protein-4 (BMP-4), vascular endothelial growth factor (VEGF-A) and mitochondrial uncoupling protein (UCP1) wherein said enhanced expression of secreted factors that selectively recruit brown adipose tissue (BAT) is remarkably more enhanced when forskolin is administered (brought into contact) to pre-adipocytes than to mature adipocytes. In other words, forskolin treated pre-adipocytes are selectively able to differentiate into BAT.

The present invention fulfils the aforesaid objectives and provides further related advantages.

SUMMARY OF THE INVENTION

The present invention discloses, (A) The ability of forskolin to prevent the formation of lipids within adult adipocytes during the differentiation of pre-adipocytes to adipocytes wherein the adipogenesis (fat deposition) inhibition is remarkably more enhanced when forskolin is administered (brought into contact) to pre-adipocytes than to mature adipocytes;

(B) The ability of forskolin to enhance the expression of secreted factors that selectively recruit brown adipose tissue (BAT) like bone morphogenetic protein-7 (BMP-7), bone morphogenetic protein-4 (BMP-4), vascular endothelial growth factor-A (VEGF-A) and mitochondrial uncoupling protein (UCP1) wherein said enhanced expression of secreted factors that selectively recruit brown adipose tissue (BAT) is remarkably enhanced when forskolin is administered (brought into contact) to pre-adipocytes than to mature adipocytes. In other words, forskolin treated pre-adipocytes are selectively able to differentiate into BAT.

The advantages of the present invention includes the demonstration of a method to achieve mammalian energy balance using forskolin on a particular physiological and developmental stage of the mammalian cellular system wherein forskolin evinces increased potential to (i) inhibit adipogenesis; and (ii) enhance the expression of secreted factors that selectively recruit brown adipose tissue (BAT) like bone morphogenetic protein-7 (BMP-7), bone morphogenetic protein-4 (BMP-4), vascular endothelial growth factor-A (VEGF-A) and mitochondrial uncoupling protein (UCP1) when brought into contact or administered to pre-adipocytes rather than to mature adipocytes.

Other features and advantages of the present invention will become apparent from the following more detailed description, taken in conjunction with the accompanying images, which illustrate, by way of example, the principle of the invention.

DETAILED DESCRIPTION OF THE MOST PREFERRED EMBODIMENTS

FIGS. 1, 2, 3 and 4

Figure 1:
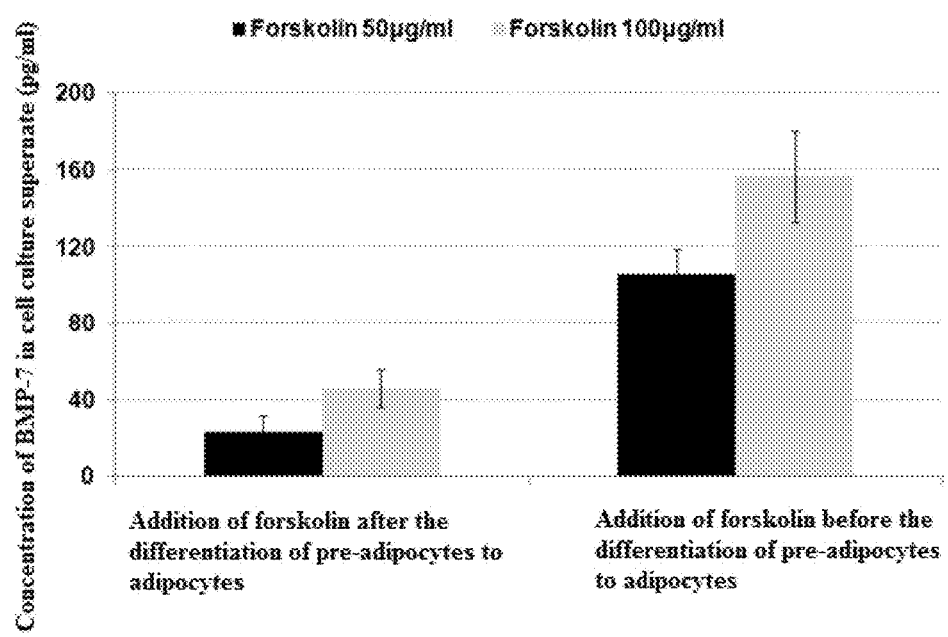
FIG. 1 shows the graphical representation of BMP-7 in cell culture supernatant of cultured 3T3-L1 adipocytes when forskolin (50 µg/ml and 100 µg/ml) are respectively added before the differentiation of pre-adipocytes to adipocytes and after the differentiation of pre-adipocytes to adipocytes.

In the most preferred embodiment, the present invention relates to a method of achieving mammalian energy balance using forskolin in a process of adipogenesis inhibition wherein forskolin is added separately to pre-adipocytes before differentiation and also to mature adipocytes to comparatively evaluate adipogenesis inhibition potential of, said process comprising steps of:

a) Seeding mammalian adipocyte precursor cells (pre-adipocytes) in wells of microplates wherein approximately 60×10⁴ cells are seeded for 48-72 hours to get 70-80% confluence;
b) Adding forskolin at concentrations of 50 µg/ml and 100 µg/ml in the pre-seeded microplates of step a consisting of undifferentiated pre-adipocytes;
c) Adding 200 µl of freshly prepared Adipogenesis induction medium to the wells;
d) Adding 200 µl of freshly prepared Adipogenesis progression medium after 72 hours of incubation with the Adipogenesis induction medium in step c;
e) Incubating the cells treated with forskolin (step b), adipogenesis induction medium (step c) and adipogenesis progression medium (step d) for 48 hours in a humidified atmosphere (37 deg. C.) of 5% CO2 and 95% air;
f) Fixing, the cells of step e by adding 100 µl of 10% formalin and staining using the Oil Red O technique;
g) Reading the optical density of cells of step f at 492 nm in a microplate reader and expressing the results as inhibitory concentration (IC50) values using the graph pad prism software;
h) Calculating the percentage inhibition of adipogenesis in the cells of steps f and g using the formula, C-T/T× 100, wherein C is the absorbance of Oil Red O in differentiating/undifferentiated cells and T is the absorbance of Oil Red O in sample treated differentiating/undifferentiated cells.
i) Adding 200 µl of freshly prepared Adipogenesis induction medium to the wells of step a.
j) Adding 200 µl of freshly prepared Adipogenesis progression medium comprising graded concentrations of forskolin (50 µg/ml and 100 µg/ml respectively) to the wells of step i after 72 hours of incubation with the Adipogenesis induction medium;
k) Incubating the cells treated with forskolin (step j), adipogenesis induction medium (step i) and adipogenesis progression medium (step j) for 48 hours in a humidified atmosphere (37 deg. C.) of 5% (CO2 and 95% air;
l) Fixing the cells of step 1 by adding 100 µl of 10% formal in and staining using the Oil Red O technique;
m) Reading the optical density of cells of step m at 492 nm in as microplate reader and expressing the results as inhibitory concentration (IC50) values using the graph pad prism software;
n) Calculating the percentage inhibition of adipogenesis in the cells of steps m and n using the formula, C-T/T×100, wherein C is the absorbance of Oil Red O in differentiating/undifferentiated cells and T is the absorbance of Oil Red O in sample treated differentiating/undifferentiated cells; and
o) Comparing percentage inhibition of adipogenesis in the cells of steps h and o.

In another most preferred embodiment, the present invention also relates to a method of mammalian energy balance using forskolin in a process of promoting the expression of secreted factors that selectively recruit brown adipose tissue (BAT) like bone morphogenetic protein-7 (BMP-7), bone morphogenetic protein-4 (BMP-4), vascular endothelial growth factor-A (VEGF-A) and mitochondrial uncoupling protein (UCP1) wherein said expression of secreted factors that selectively recruit brown adipose tissue (BAT) is remarkably enhanced as measured when forskolin is administered (brought into contact) to pre-adipocytes than to mature adipocytes, said method incorporating the steps of, a) Seeding mammalian adipocyte precursor cells (pre-adipocytes) in wells of microplates wherein approximately 60×10⁴ cells are seeded for 48-72 hours to get 70-80% confluence;
b) Adding forskolin at concentrations of 50 µg/ml and 100 µg/ml in the pre-seeded microplates of step a consisting of undifferentiated pre-adipocytes;
c) Adding 200 µl of freshly prepared Adipogenesis induction medium to the wells;
d) Adding 200 µl of freshly prepared. Adipogenesis progression medium after 72 hours of incubation with the Adipogenesis induction medium in step c;
e) Incubating the cells treated with forskolin (step b), adipogenesis induction medium (step c) and adipogenesis progression medium (step d) for 48 hours in a humidified atmosphere (37 deg. C.) of 5% CO2 and 95% air;
f) Quantitatively determining by appropriate immunoassay techniques the expressions of BMP-7, BMP-4, VEGF-A and UCP-1 in the cell supernatant;
g) Adding 200 µl of freshly prepared Adipogenesis induction medium to the wells of step a;
h) Adding 200 µl of freshly prepared Adipogenesis progression medium comprising graded concentrations of forskolin (50 µg/ml and 100 µg/ml respectively) to the wells of step g after 72 hours of incubation with the Adipogenesis induction medium;
i) Incubating the cells treated with forskolin (step h), adipogenesis induction medium (step g) and adipogenesis progression medium (step h) for 48 hours in a humidified atmosphere (37 deg. C.) of 5% CO2 and 95% air; and
j) Quantitatively determining by appropriate immunoassay techniques the expressions of BMP-7, BMP-4, VEGF-A and UCP-1 in the cell supernatant.

In yet another most preferred embodiment, the present invention relates to a method of achieving energy balance in mammalian adipose cellular systems, said method comprising step of administering forskolin in effective amounts targeted towards mammalian pre-adipocytes to achieve effects of (a) increased inhibition of adipogenesis and (b) increased expression of secretory factors that function individually or in combination to specifically recruit brown adipocytes or brown like (beige or brite) adipocytes. In specific embodiments, the secretory factors are selected from the group consisting of bone morphogenetic protein-7 (BMP-7), bone morphogenetic protein-4 (BMP-4), vascular endothelial growth factor-A (VEGF-A) and mitochondrial uncoupling protein (UCP1).

In yet another most preferred embodiment, the invention pertains to forskolin for use in therapy for obesity wherein said therapy involves achieving energy balance in mammalian adipocytes by administering forskolin in effective amounts targeted towards mammalian pre-adipocytes to bring about the effects of (a) increased inhibition of adipogenesis and (b) increased expression of secretory factors that function individually or in combination to specifically recruit brown adipocytes or brown like (beige or brite) adipocytes. In specific embodiments, the secretory factors are selected from the group consisting of bone morphogenetic protein-7 (BMP-7), bone morphogenetic protein-4 (BMP-4), vascular endothelial growth factor-A (VEGF-A) and mitochondrial uncoupling protein (UCP1)

In yet another most preferred embodiment, the present invention relates to a method to induce the brown like phenotype (beige or brite adipocytes) in white adipocyte depots in mammals said method comprising step of administering effective amount of forskolin to obese mammals with depots of fully differentiated white adipocytes to achieve effect of increase in secretory factors that bring about the development of brown like phenotype (beige or brown adipocytes) within white adipocyte depots. In specific embodiment, the secretory factors are vascular endothelial growth factor-A (VEGF-A) and mitochondrial uncoupling protein (UCP1). In yet another most preferred embodiment, the present invention relates to Forskolin for use in the therapy of obesity characterised in that forskolin is administered in effective amounts targeting mammalian white adipocyte depots to achieve effect of increased expression of secretory factors vascular endothelial growth factor-A (VEGF-A) and mitochondrial uncoupling protein (UCP1) that cause the development of brown like phenotype (beige or brite adipocytes) in white adipocyte depots in mammals.

In yet another most preferred embodiment, the present invention relates to a method of achieving energy balance in mammalian adipose cellular systems, said method comprising step of administering forskolin in effective amounts targeted towards mammalian pre-adipocytes to bring about of the effect of enhanced expression of mitochondrial uncoupling protein 1 (UCP-1) to result in increased mitochondrial thermogenesis in differentiated brown adipocytes and brown like (beige or brite) adipocytes.

In an alternative embodiment, the present invention also relates to forskolin for use in therapy for obesity wherein said therapy involves achieving energy balance in mammalian adipocytes by administering forskolin in effective amounts targeted towards mammalian pre-adipocytes to bring about the effects of enhanced expression of secretory factor mitochondria uncoupling protein 1 (UCP-1) to result in increased mitochondrial thermogenesis in differentiated brown adipocytes and brown like (beige or brite) adipocytes.

Illustrative Examples

As illustrative examples of the most referred embodiments outlined herein above, the following results are presented to show that forskolin when administered in increasing concentration is more effective in (a) preventing adipogenesis and (b) also in promoting the expression of secreted factors like BMP7, BMP-4, VEGF-A and UCP-1 that recruit the brown adipocytes thereby creating energy balance in mammalian cell systems, when administered at the pre-adipocyte stage than one the transformation of pre-adipocytes to adipocytes has occurred.
Result 1—Prevention of Adipogenesis

TABLE A

| CONCEN-TRATION ($\mu$g/ml) | % inhibition of adipogenesis when forskolin is added at the pre-adipocyte stage (before differentiation into the adipocyte stage) | % inhibition of adipogenesis when forskolin is added after differentiation of pre-adipocytes to the adipocyte stage |
|---|---|---|
| 6.25 | 10.2 | 1.2 |
| 12.50 | 12.8 | 6.8 |
| 25 | 19.7 | 10.6 |
| 50 | 35.5 | 12.9 |
| 100 | 41.8 | 18.5 |

Table A shows that at each tested concentration of forskolin, the administration of forskolin at the mammalian pre-adipocyte stage has as profound effect on preventing adipogenesis that when administered after the differentiation of pre-adipocytes to adipocytes. Double or more than double the % inhibition of adipogenesis was observed when forskolin was administered at the pre-adipocyte stage as compared to administration at the adipocyte stage.
Result 2—Expression of Secretor Proteins that Recruit Brown Adipocytes
  A. BMP-7
  The biological role of BMP-7 as a recruiter of the brown adipocyte lineage has been discussed in the following scientific literature.
    1. Mathew Harms and Patrick Scale, "Brown and beige fat: development, function and therapeutic potential", Nature Medicine, Volume 19, Number 10, October 2013, pages 1252-1263;
    2. BMP7 Activates Brown Adipose Tissue and Reduces Diet-Induced Obesity at Sub thermoneutrality. Mariëtte R. Boon Published: Sep. 16, 2013; PLOS One.
    3. New role of bone morphogenetic protein 7 in brown adipogenesis and energy expenditure. Tseng et al. Nature, 2008 Aug. 21; 454(7207):1000-4. doi: 10.10381/nature07221.
    4. Transcriptional Control of Brown Fat Development; Kajimure et al. Cell Metabolism; Volume 11, Issue 4, 7 Apr. 2010, Pages 257-262.

Immunoassays (Enzyme linked immunosorbent assay) for the quantification of BMP-7 in the cell culture supernatant when forskolin (50 $\mu$g/ml and 100 $\mu$g/ml) was administered at the pre-adipocyte stage and once the differentiation to adipocytes occurred indicated that forskolin profoundly increased BMP-7 expression in at the pre-adipocyte stage than at the adipocyte stage.

Thus, in correlation with the literature cited above, it may be deduced that forskolin evinces greater potential for brown fat conversion of pre-adipocytes (FIG. 1) rather than fully differentiated white adipocytes. The example exemplified by FIG. 1 provides substantiation to the disclosed most preferred embodiment that forskolin directs the selective differentiation of mammalian pre-adipocytes to brown adipocytes by allowing the expression of secretory factor BMP-7.
  B. BMP-4
  Acting along with BMP-7, BMP-4 is a new adipokine and acts on adipogenesis and white to brown transition (Qian S W et al Proc Natl Acad Sci USA 110: E798-807, 2013). Immunoassays (Enzyme linked immunosorbent assay) for the quantification of BMP-4 in the cell culture supernatant when forskolin (50 $\mu$g/ml and 100 $\mu$g/ml) was administered at the pre-adipocyte stage and once the differentiation to adipocytes occurred indicated that forskolin profoundly increased BMP-4 expression in at the pre-adipocyte stage than at the adipocyte stage.

Figure 2:
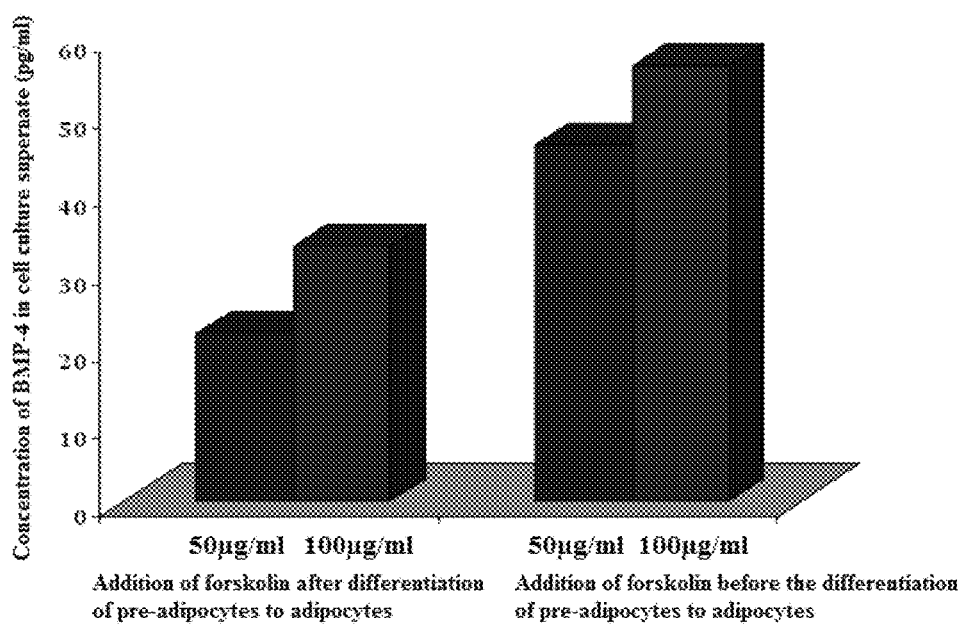
FIG. 2 shows the graphical representation of BMP-4 in cell culture supernatant of cultured 3T3-1 adipocytes when forskolin (50 µg/ml and 100 µg/ml) are respectively added before the differentiation of pre-adipocytes to adipocytes and after the differentiation of pre-adipocytes to adipocytes.
Figure 3:
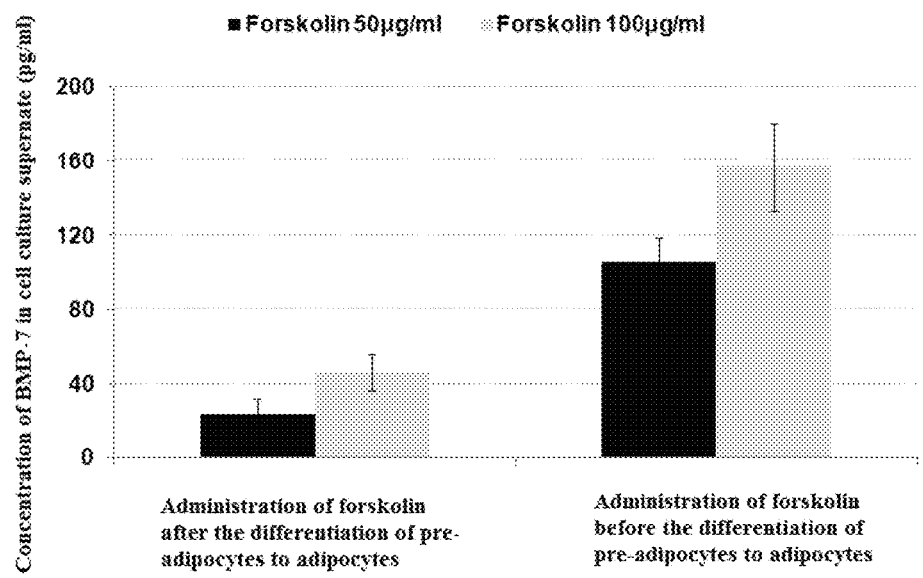
FIG. 3 shows the graphical representation of VEGF-A in cell culture supernatant of cultured 3T3-L1 adipocytes when forskolin (50 g/ml and 100 µg/ml) are respectively added before the differentiation of pre-adipocytes to adipocytes and after the differentiation of pre-adipocytes to adipocytes.

Thus, in correlation with the literature cited above, it may be deduced that forskolin evinces greater potential for conversion of white pre-adipocytes to the brite/beige adipocyte (brown adipocyte like) (FIG. 2) by the combined increased expressions and biological actions of secretory factors BMP-4 and BMP-7. The example exemplified by FIG. 2 provides substantiation to the most preferred embodiment that forskolin brings about the transformation of white pre-adipocytes to brite or beige adipocytes.
  C. VEGF-A
  VEGF-A over expression leads to an increase in brown adipose tissue (BAT) thermogenesis and also promotes a "BAT-like" phenotype in white adipose tissue depots. In diet-induced obese mice, introducing VEGF-A locally in BAT rescues capillary rarefaction, ameliorates brown adipocyte dysfunction, and improves deleterious effects on glucose and lipid metabolism caused by a high-fat diet challenge. These results demonstrate as direct positive role of VEGF-A in the activation and expansion of BAT.

VEGF-A over expression also exerts its action on macrophages by increasing the recruitment of M2 anti-inflammation, macrophages to fat depots. The decreased obesity and the anti-inflammatory milieu induced by VEGF-A in adipose tissue is responsible for the reduction of insulin resistance in transgenic mice (Bagchi et at "Vascular endothelial growth factor is important for brown adipose tissue development and maintenance", *FASEB J.* 27, 3257-3271 (2013). Immunoassays (Enzyme linked immunosorbent assay) for the quantification of VEGF-A in the cell culture supernatant when forskolin (50 µg/ml and 100 µg/ml) was administered at the pre-adipocyte stage and once the differentiation to adipocytes occurred indicated that forskolin profoundly increased VEGF-A expression in the pre-adipocyte stage than at the adipocyte stage. Thus, in correlation with the literature cited above, it may be deduced that forskolin evinces greater potential for conversion of white pre-adipocytes to the brown adipocyte like (brite or beige) cells (FIG. 3) among white adipocyte depots in the mammalian body.

D. Uncoupling Protein-1 (UCP-1)

Figure 4:
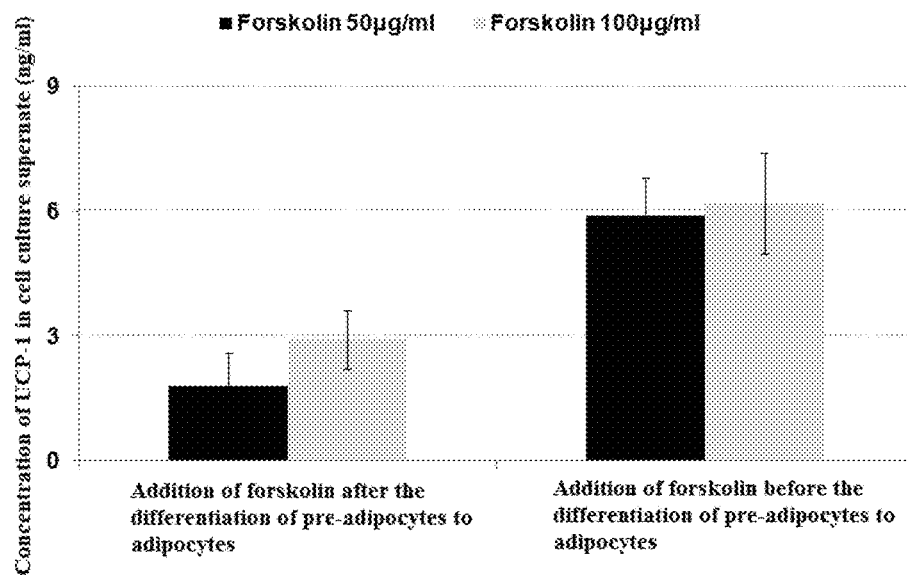
FIG. 4 shows the graphical representation of UCP1 in cell culture supernatant of cultured 3T3-L1 adipocytes when forskolin (50 µg/ml and 100 µg/ml) are respectively added before the differentiation of pre-adipocytes to adipocytes and after the differentiation of pre-adipocytes to adipocytes.

A system of thermogenesis that evolved to protect the body from hypothermia is based upon the uncoupling of oxidative phosphorylation in brown adipocytes by the mitochondrial uncoupling protein (UCP-1). It has been shown that up-regulation of UCP1 by genetic manipulations or pharmacological agents can reduce obesity and improve insulin sensitivity (International Journal of Obesity (2008) 32, S32-S38 doi:10.1038/ijo.2008.236 UCP1: its involvement and utility in obesity. L P Kozak and R Anunciado-Koza). Immunoassays (Enzyme linked immunosorbent assay) for the quantification of UCP-1 in the cell culture supernatant when forskolin (50 µg/ml and 100 µg/ml) was administered at the pre-adipocyte stage and once the differentiation to adipocytes occurred indicated that forskolin profoundly increased UCP-1 expression in the pre-adipocyte stage than at the adipocyte stage. Thus, in correlation with the literature cited above, it may be deduced that forskolin evinces greater potential for conversion of pre-adipocytes to the BAT-like or brown adipocytes and enhanced UCP-1 expression in these cells can be expected to enhance bringing about energy balance through appropriate energy expenditure (FIG. 4).

It is already reported that administration of forskolin in humans apparently does not cause clinically significant side effects (Shonteh Henderson et al, Effect of Coleus forskolin supplementation on body composition and haematological profiles in mildly overweight women, J Int Soc Sports Nutr. 2005, 2(2); 54-62). The study elucidates that supplementation with forskolin dietary supplement Forslean®) [250 mg of 10% Coleus forskolin extract, 25 mg of forskolin] two times a day for 12 weeks apparently had no clinical side effects. It may thus be inferred that the illustrative in-vitro examples included herein above to achieve energy balance in mammalian adipocyte systems is also applicable in vivo studies in animals (mammals) including human beings.

Although the foregoing invention has been described in some detail by way of illustration and example for purposes of clarity of understanding, it will be obvious that certain changes and modifications may be practiced within the scope of the appended claims.

We claim:

1. A method of mammalian energy balance using forskolin in a process of promoting the expression of secreted factors that selectively recruit brown adipose tissue (BAT), said method comprising:
   a) Seeding mammalian adipocyte precursor cells (pre-adipocytes) in wells of microplates wherein approximately $60 \times 10^4$ cells are seeded for 48-72 hours to get 70-80% confluence;
   b) Adding forskolin at concentrations of 50 µg/ml and 100 µg/ml in the pre-seeded microplates of step a consisting of undifferentiated pre-adipocytes and thereafter incubating the pre-adipocytes for 72 hours in a medium added to the wells of the microplates to form cells treated with forskolin;
   c) Incubating the cells treated with forskolin in step b for 48 hours in a humidified atmosphere at 37° C. with 5% $CO_2$ and 95% air; and
   d) Quantitatively determining by immunoassay techniques the expressions of bone morphogenetic protein-7 (BMP-7), bone morphogenetic protein-4 (BMP-4), and vascular endothelial growth factor-A (VEGF-A) in the cell supernatant; wherein
      the secreted factors that selectively recruit brown adipose tissue (BAT) comprise one or more members selected from the group consisting of BMP-7, BMP-4, and VEGF-A, and
      the expression of the secreted factors that selectively recruit brown adipose tissue (BAT) is enhanced as measured when forskolin is administered to pre-adipocytes compared to mature adipocytes.

2. A method comprising administering forskolin in effective amounts to mammalian white pre-adipocytes to achieve a transformation of the white pre-adipocytes into brite or beige adipocytes, wherein
   the mammalian white pre-adipocytes are administered forskolin by incubating the mammalian white pre-adipocytes with forskolin for at least a period of 72 hours, and the administration of the forskolin results in the increased expression of at least one secretory factor selected from the group consisting of bone morphogenetic protein-7 (BMP-7), bone morphogenetic protein-4 (BMP-4), and vascular endothelial growth factor-A (VEGF-A).

3. The method according to claim 2, wherein the administration of the forskolin results in the increased expression of vascular endothelial growth factor-A (VEGF-A).

4. The method according to claim 2, wherein the administration of the forskolin results in the increased expression of secretory factors that function in combination, the secretory factors comprising bone morphogenetic protein-7 (BMP-7), bone morphogenetic protein-4 (BMP-4), and vascular endothelial growth factor-A (VEGF-A).

5. The method according to claim 2, wherein the administration of the forskolin results in the increased expression of bone morphogenetic protein-7 (BMP-7).

6. The method according to claim 2, wherein the administration of the forskolin results in the increased expression of bone morphogenetic protein-4 (BMP-4).

7. The method according to claim 2, wherein the administration of the forskolin results in the increased expression of secretory factors that function in combination, the secretory factors comprising bone morphogenetic protein-7 (BMP-7) and bone morphogenetic protein-4 (BMP-4).

* * * * *